United States Patent [19]

Kwun et al.

[11] Patent Number: 4,711,120
[45] Date of Patent: Dec. 8, 1987

[54] METHOD OF WEAR MONITORING USING ULTRASONIC PHASE COMPARISON

[75] Inventors: Hegeon Kwun; Anmol S. Birring; Gurvinder P. Singh; Gary J. Hendrix; David G. Alcazar, all of San Antonio, Tex.

[73] Assignee: Association of American Railroads, Washington, D.C.

[21] Appl. No.: 915,382

[22] Filed: Oct. 6, 1986

[51] Int. Cl.$^4$ .......................................... G01M 15/00
[52] U.S. Cl. .................................................. 73/119 R
[58] Field of Search ................. 73/118.1, 117.3, 117.2, 73/116, 119 R, 597, 614, 615; 340/52 R, 52 T

[56] References Cited

U.S. PATENT DOCUMENTS

| | | | |
|---|---|---|---|
| 2,474,320 | 6/1949 | Pelan | 73/119 R |
| 3,365,664 | 1/1968 | Weigert | 368/120 |
| 3,783,681 | 6/1974 | Hirt et al. | 73/119 R |
| 3,895,294 | 7/1975 | Vinding | 324/83 D |
| 3,906,361 | 9/1975 | Nessler et al. | 324/83 D |
| 3,918,296 | 11/1975 | Kitada | 73/627 |
| 3,994,154 | 11/1976 | Niklas et al. | 73/597 |
| 4,068,210 | 1/1978 | Corkhill | 367/190 |
| 4,102,205 | 7/1978 | Pies et al. | 73/614 |
| 4,123,943 | 11/1978 | Roddy et al. | 73/597 |
| 4,254,660 | 3/1981 | Prause | 73/597 |
| 4,307,611 | 12/1981 | Opara | 73/597 |
| 4,398,420 | 8/1983 | Haesen et al. | 73/597 |
| 4,437,332 | 3/1984 | Pittaro | 73/1 DV |
| 4,510,793 | 4/1985 | Ploegaert et al. | 73/597 |
| 4,542,652 | 9/1985 | Reuter et al. | 73/597 |
| 4,545,248 | 12/1985 | Kitada et al. | 73/597 |
| 4,545,249 | 10/1985 | Matay | 73/597 |
| 4,567,766 | 2/1986 | Seiferling | 73/597 |
| 4,624,142 | 11/1986 | Heyman | 73/597 |

FOREIGN PATENT DOCUMENTS 419758 3/1974 U.S.S.R. .................. 73/118.1

Primary Examiner—Stewart J. Levy
Assistant Examiner—Robert R. Raevis
Attorney, Agent, or Firm—Antonelli, Terry & Wands

[57] ABSTRACT

A method of monitoring the cylinder wall wear using ultrasonic phase comparison techniques is disclosed. The method comprises the steps of introducing ultrasonic waves in a cylinder wall so that the waves travel through the cylinder wall. A change in the traveling time of the ultrasonic waves traveling through the cylinder wall due to cylinder wall wear is determined. The amount of wear of the cylinder wall is calculated by multiplying the velocity of the ultrasonic waves in the cylinder wall by the traveling time change due to cylinder wall wear. The traveling time change due to cylinder wall wear is obtained by determining the actual change in travel time by a phase comparison of the traveling ultrasonic waves and adjusting the actual change in travel time to compensate for any change due to temperature variation of the cylinder wall. With this method, small changes in traveling time on the order of $10^{-11}$ second can be determined so that thickness changes due to wear on the order of $5 \times 10^{-4}$ mm are possible.

11 Claims, 2 Drawing Figures

METHOD OF WEAR MONITORING USING ULTRASONIC PHASE COMPARISON

BACKGROUND AND SUMMARY OF THE INVENTION

The present invention is directed to a method of monitoring cylinder wall wear of an internal combustion engine. The method involves the introduction of ultrasonic waves in the cylinder wall for detecting minute changes in the thickness of the cylinder wall resulting from wear.

Cylinder wall wear in an internal combustion engine occurs during the use of the engine due to the sliding contact of the piston and rings thereon against the adjacent cylinder wall. When the wear becomes excessive, the operating efficiency of the engine can be substantially reduced and/or cylinder wall failure can occur thereby rendering the engine inoperative. When the engine is rendered inoperative at an unexpected time, serious economic problems and possible human safety problems can arise, depending upon the application of the internal combustion engine. In large diesel engines in locomotives, for example, an entire train can be stranded on the tracks until emergency service is made available. Failure of the engine in an airplane can be catastrophic.

One attempt to avoid breakdowns due to engine cylinder wall failure is to periodically replace or overhaul the engine cylinder wall as by replacing a cylinder liner therein, after a fixed period of engine use, e.g., hours of engine operation, miles traveled, or other indicator. However, one problem associated with this proposed solution is that the fixed number of hours of operation or mileage before engine overhaul or replacement is an average figure, so that some engines will be overhauled or replaced prematurely while others may still fail before they are due for servicing or replacement. Instances of this last mentioned case increase the cost of operation of the motor driven device and are therefore undesirable.

An object of the present invention is to provide a method of monitoring cylinder wear which overcomes the aforementioned disadvantages associated with the operation and use of internal combustion engines. The method involves introducing ultrasonic waves in a cylinder wall of the engine, so that the waves travel through the cylinder wall.

It has been proposed in U.S. Pat. No. 4,123,943 to introduce ultrasonic waves in an engine cylinder so that the waves travel through the cylinder wall for the purpose of measuring cylinder wall thickness prior to machining the cylinder wall. This known method involves immersing the body in a coupling fluid, generating an ultrasonic signal within the cylinder bore and sensing signal reflections from the inner and outer wall surfaces. High frequency pulses are counted between the occurrence of a pulse and receipt of the first and second reflected pulses. The count is adjusted for differences in the velocity of sound in the different media to determine the thickness of the engine cylinder wall.

This known method is not suitable for use in an engine once it has been assembled and is operating in its intended environment because of the requirement for immersing the body in a coupling fluid. Moreover, this known method relates to the measurement of absolute thickness and the accuracy of the measurement is at best on the order of 0.01 mm.

U.S. Pat. No. 4,510,793 discloses a method of monitoring the wear of a refractory lining of a metallurgical furnace wall which involves the steps of arranging a bar of ceramic material in a hole drilled in the refractory lining, so that the bar has an inner end at the inner face of the lining and extends to the exterior of the wall. The bar is thus subjected to wear at its inner end as the lining wears. The position of the worn inner end of the bar is determined ultrasonically by generating ultrasonic pulses in the bar and detecting the reflecting of the pulses from the worn inner end of the bar. The conventional traveling time measurement technique is likewise employed for measuring the wear as the desired accuracy is only about 1 to 2 cm according to the patent.

A further object of the present invention is to provide a method of monitoring engine cylinder wall wear which avoids the aforementioned disadvantages with the prior art methods referred to such that the wear of the engine can be monitored continuously, if desired, throughout the life of the engine and with a high degree of accuracy so that thickness changes on the order of 0.0001 mm can be detected, and without necessitating drilling a hole through the cylinder wall or the use of special bar positioned within such a hole.

These and other objects are attained by the method of monitoring cylinder wall wear according to the present invention. As noted above, the method comprises the step of introducing ultrasonic waves in an engine cylinder wall, so that the waves travel through the cylinder wall. Further, the method includes the steps of determining a change in the traveling time of the ultrasonic waves traveling through the cylinder wall due to cylinder wall wear. The amount of wear of the cylinder wall is then calculated by multiplying the velocity of the ultrasonic waves in the cylinder wall by the traveling time change due to cylinder wall wear.

According to a disclosed preferred embodiment of the method, the change in the traveling time of the ultrasonic waves traveling through the cylinder wall due to cylinder wall wear is determined by using the phase comparison technique (For example, R.J. Blume, Rev. Sci. Instrum. 34, 1400 (1963); H. KWUN, J. Appl. Phys. 57, 1555 (1985)). The phase comparison technique enables small changes in traveling time of the waves on the order of $10^{-11}$ second to be determined. More specifically, the change in travel time due to wear is determined by measuring the resulting change in the phase of the travelling ultrasonic waves. As the velocity of ultrasonic waves in the cylinder wall depends on the temperature of the cylinder wall, the actual change in travel time must be adjusted to compensate for any change in travel time due to temperature variation of the cylinder wall to obtain travel time change due to wear. The temperature of the engine cylinder wall is monitored according to the method of the invention to enable compensation for travel time change due to temperature variation.

In the disclosed embodiment of the invention, the ultrasonic waves are introduced at or near an outer peripheral surface of a liner by means of an ultrasonic transducer. The ultrasonic waves transmitted by the transducer travel to the inner surface of the cylinder wall and are reflected back toward the outer peripheral surface thereof where they are detected by the same or a separate ultrasonic transducer. With the method of the invention, the wear of the liner of internal combustion engine can be monitored continuously during operation of the engine.

These and other objects, features and advantages of the present invention will become more apparent from the following description when taken in connection with the accompanying drawings which show, for purposes of illustration only, one preferred embodiment in accordance with the present invention.

DETAILED DESCRIPTION OF THE DISCLOSED EMBODIMENT

Figure 1:
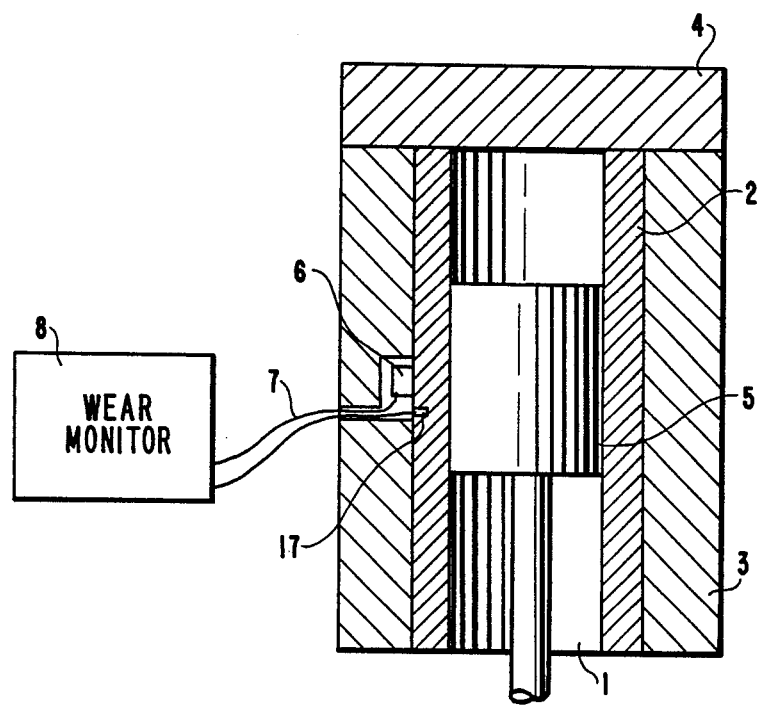
FIG. 1 is a cross-sectional view through a cylinder of an internal combustion engine whose wear is to be monitored according to the present invention.

Referring now to the drawings, an arrangement for monitoring the wear of a cylinder 1 of an internal combustion engine according to the method of the invention is illustrated in FIG. 1. The cylinder 1 of the engine has a cylinder wall which is formed by a liner 2 positioned within an engine block 3. The cylinder is closed at one end with a head 4 of the engine. A piston 5 is located within the cylinder for reciprocation during operation of the engine.

The method of the invention for monitoring wear of the cylinder wall or liner 2 comprises the step of introducing ultrasonic waves in the cylinder wall. For this purpose, in the illustrated embodiment an ultrasonic probe 6 is bonded to the outer peripheral surface of the liner 2 of the cylinder. To maintain a good solid bond between the ultrasonic probe 6 and the liner in high temperature and vibrational environment, the probe 6 is soldered or brazed to the liner 2 of the, cylinder 1. The probe 6 is connected by an electrical connection 7 to the ultrasonic wear monitor apparatus 8 of the invention. The ultrasonic probe 6 comprises both a transmitter 9 and a receiver 10, for respectively transmitting and receiving ultrasonic energy. When acting as a transmitter, the probe 6 is supplied with a short pulse of a high frequency electrical signal by a signal generator 11 and a gated amplifier 12. The signal generator 11 produces a continuous sinusoidal wave of a fixed frequency. The frequency of the electrical signal from the signal generator 11 is accurately controlled to a frequency of 1 Hz, for example. The gated amplifier 12 gates a portion of the continuous wave from the signal generator 11 and amplifies the gated signal. A typical gate width used is about 1~2 μsec. When monitoring wear during operation of the engine, it is preferred to match the repetition rate of the gated amplifier 12 to the rpm of the engine and synchronize the triggering of the gated amplifier 12 to the motion of the piston 5. As will be readily apparent to the skilled artisan, this matching and synchronism could be accomplished, for example, by providing a small magnet on the engine flywheel at a selected angular position and providing an electrical coil adjacent the flywheel so that the magnet induces an electrical signal for triggering the gated amplifier 12 at a predetermined time during each revolution of the engine, such as at a time corresponding to the bottom dead center position of the piston. The gated and amplified signal is applied to the probe 6 which acts as the transmitter 9 and changes the electrical signal to mechanical vibration for introducing ultrasonic waves in the liner. The ultrasonic waves introduced at the liner 2 of the cylinder travel to the inner peripheral surface of the liner where they are reflected back to the ultrasonic probe 6. The reflected waves are converted back to an electrical signal by the probe 6 which now acts as the ultrasonic receiver 10.

The method of monitoring cylinder wall wear of the invention further includes the step of determining a change in the traveling time of the ultrasonic waves traveling through the cylinder wall due to cylinder wall wear. That is, the time required for the ultrasonic waves to travel from the ultrasonic probe 6 to the inner peripheral wall of the cylinder wall and upon being reflected to travel back to the ultrasonic probe 6 will be reduced as the cylinder wall is worn by contact with the reciprocating piston 5 therein. The amount of wear of the cylinder wall is then calculated according to the method by multiplying the known velocity of the ultrasonic waves in the cylinder wall by the traveling time change due to cylinder wall wear. Thus, a change in thickness, e.g., the amount of wear of the cylinder wall, is determined, rather than the total thickness.

Figure 2:
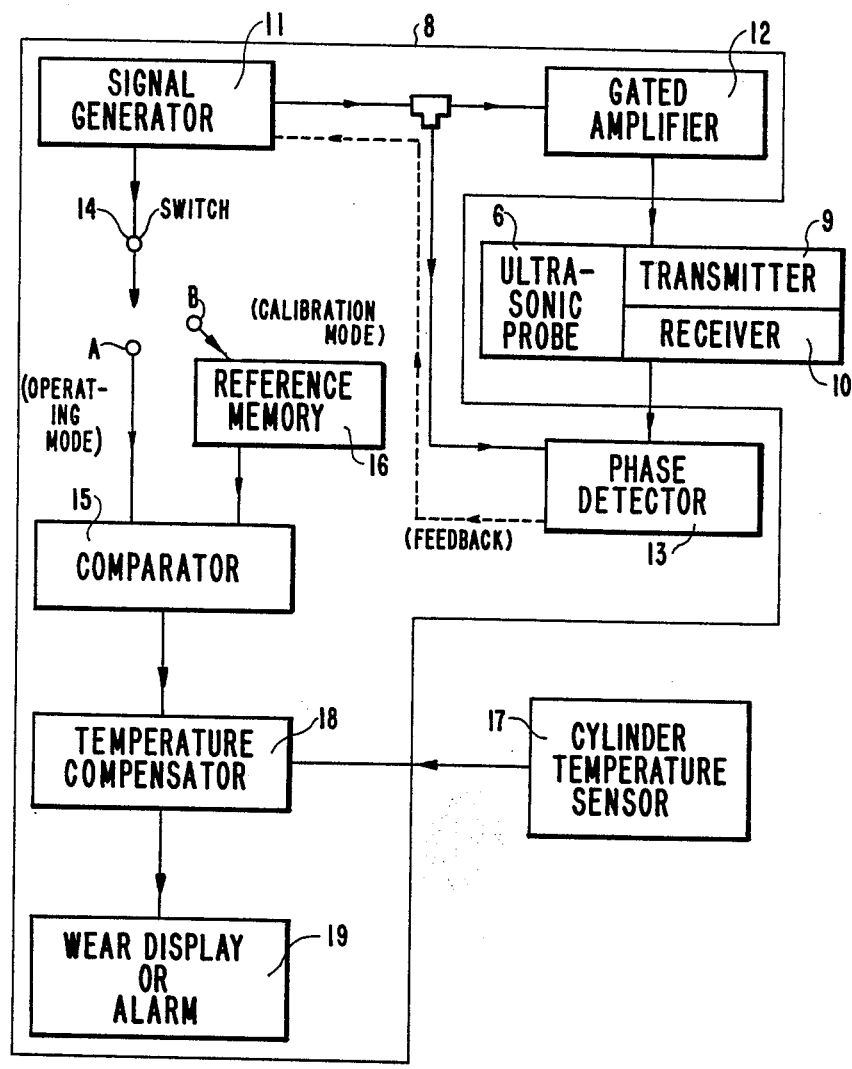
FIG. 2 is a circuit diagram of the wear monitor schematically illustrated in FIG. 1 for practicing the method of the present invention.

The change in the traveling time of the ultrasonic waves traveling through the cylinder wall due to cylinder wall wear is determined by using the phase comparison technique. More particularly, as illustrated in FIG. 2 of the drawings, the wear monitor apparatus 8 of the invention includes a phase detector 13. The phase of the detected ultrasonic wave with respect to the phase of the continuous wave signal from the signal generator 11 is measured by the phase detector 13 which gives a good accuracy of the difference in phase between the two signals, for example, within 0.1 degree where the signal generator drives the ultrasonic transmitter at a frequency of 10 MHz. Typically, the two signals are set to a null relative phase condition by adjusting the frequency of the signal generator 11. Any small changes in travel time will cause the phase of the detected ultrasonic wave to deviate from the preset null condition. Using a feedback loop, the output of the phase detector 13 is used to readjust the frequency of the signal generator 11 to maintain the null condition. The change in travel time $\Delta t$ is then given by $\Delta t = -t\,(f/f)$ where t is the initial travel time, f is the frequency for the initial null condition and $\Delta f$ is the difference between the frequencies at the initial and the new null conditions. The change in travel time is therefore determined by measuring the changes in the frequency of the signal generator 11 required to maintain the null phase condition. The phase comparator may be a multiperiodical phase meter of the type shown in U.S. Pat. No. 4,157,500, for example. Digital phase measuring systems are also known from U.S. Pat. No. 3,906,361. The use of a phase comparator in distance measuring apparatus is also known from U.S. Pat. No. 3,365,664.

The frequency counter signal of the signal generator 11 of the invention is directed by a switch 14 directly to a comparator 15, when the switch 14 is in position A shown in FIG. 2 for the operating mode of the wear monitor apparatus 8. When the switch 14 is in the position B, a calibration mode the frequency counter signal is directed to a reference memory 16. The switch 14 is set at position B to obtain the frequency of the signal generator 11 at the initial null phase condition between the waveforms of the signal from the signal generator 11 and the output signal from the ultrasonic receiver 10 in the case of a new engine or where a new cylinder liner 2 has been installed in an existing engine, for example. Subsequently, the switch 14 is set in the A position or operating mode. The reference frequency from the memory 16 is then supplied to the comparator 15 for measurement of changes in travel time. The comparator can measure changes in travel time at any time or continuously in the life of the engine cylinder wall subsequent to the setting of the initial null condition. The output of the comparator thus corresponds to a change in the traveling time of the ultrasonic waves traveling through the cylinder liner. Small changes in traveling time on the order of $10^{-11}$ second can be determined in this manner.

Wear processes always generate heat which increases the temperature of the part. As the velocity of ultrasonic waves in a material depends on the temperature, the temperature increase of the part from such heat influences the traveling time of the ultrasonic waves. Therefore, according to the method of the invention, to determine the change in the traveling time due to wear, compensation must be made for the effect of any temperature change on the traveling time change detected in the manner described above. This is accomplished by providing a temperature sensor 17 which is attached to the liner 2 of the cylinder 1 at a location near the ultrasonic probe 6. The output signal from the sensor 17 is electrically connected to a temperature compensator 18 as shown in FIG. 2. At the temperature compensator 18, the effect of any temperature change on the traveling time is calculated and subtracted from the apparent change in the traveling time received from the comparator 15. The remaining changes in the traveling time are due to wear.

The amount of wear is then obtained by multiplying the velocity of the ultrasonic waves in the material of the liner by the determined traveling time change due to wear. This result is displayed at the wear display 19 shown schematically in FIG. 2. The wear display can be an analog display of wear thickness or a digital readout, in which case there would be an analog digital converter in the circuit. Alternatively, the wear display 19 could simply be an alarm which would be triggered after a threshold wear of the cylinder wall has been calculated to thereby indicate that it is time for replacing the cylinder liner 2, for example. With the method of the invention, thickness changes due to wear on the order of $5 \times 10^{-4}$ mm can be determined, so that the magnitude of the cylinder wall wear of the engine can be accurately determined. The method of monitoring the cylinder wall wear of the invention can be performed continuously during the operation of an engine, for example, or at intermittent times during the life thereof as noted above. Since the apparatus for performing the method of the invention can readily be integrated with the engine, it is not necessary to return to a garage or testing facility to accurately access the wearing of the engine cylinder wall and a hole does not have to be drilled completely through the cylinder wall as in the prior art wear monitoring method referred to above.

While we have shown and described only one embodiment in accordance with the present invention, it is understood that the same is not limited thereto, but is susceptible of numerous changes and modifications as known to those skilled in the art. For example, a programmed microprocessor could be used to perform the phase comparison operation of the invention described above, as well as the subsequent operations discussed. Further, the method of monitoring wear disclosed herein could be used to monitor the wear of parts other than engine cylinders. Therefore, we do not wish to be limited to the details shown and described herein, but intend to cover all such changes and modifications as are encompassed by the scope of the appended claims.

We claim:

1. A method of monitoring cylinder wall wear in an engine comprising the steps of introducing ultrasonic waves in cylinder wall of the engine at least at intermittent times during the life of the engine so that the waves travel through the cylinder wall, determining a change in the traveling time of the ultrasonic waves traveling through the cylinder wall due to cylinder wall wear by phase comparison of the traveling ultrasonic waves, and calculating the amount of wear of the cylinder wall by multiplying the velocity of the ultrasonic waves in the cylinder wall by the traveling time change due to cylinder wall wear to thereby provide an indication as to whether engine overhaul or replacement is needed.

2. A method of monitoring cylinder wall wear according to claim 1, wherein the ultrasonic waves are introduced at or near an outer peripheral surface of the cylinder wall by means of an ultrasonic transmitter which is bonded to the cylinder wall.

3. A method of monitoring cylinder wall wear according to claim 2, wherein the ultrasonic waves travel to the inner peripheral surface of the cylinder wall and are reflected back to the outer peripheral surface of the cylinder wall where they are detected by an ultrasonic receiver.

4. A method of monitoring cylinder wall wear according to claim 1, wherein the cylinder wall is a cylinder liner within an engine block of said engine.

5. A method of monitoring cylinder wall wear according to claim 1, wherein the cylinder wall surrounds a piston of said engine and wherein said introduction of said ultrasonic waves is synchronized to the motion of said piston during operation of said engine.

6. A method of monitoring cylinder wall wear according to claim 1, wherein the cylinder wall wear is monitored continuously during operation of said engine.

7. A method of monitoring cylinder wall wear according to claim 1, wherein small changes in traveling time on the order of $10^{-11}$ second are determined.

8. A method of monitoring cylinder wall wear according to claim 1, wherein the change in the traveling time due to cylinder wall wear is determined by determining an actual change in travel time of the ultrasonic waves through the cylinder wall and adjusting the actual change in travel time to compensate for any change due to temperature variation of the cylinder wall to obtain travel time change due to wear.

9. A method of monitoring cylinder wall wear according to claim 8, including the step of monitoring the temperature of the cylinder wall to enable compensation for travel time change due to temperature variation.

10. A method of monitoring cylinder wall wear according to claim 1, wherein thickness changes due to wear on the order of $5 \times 10^{-4}$ mm are determined according to the method.

11. A method of monitoring cylinder wall wear according to claim 1, wherein the phase comparison of the traveling waves includes detecting the phase of the ultrasonic waves which have traveled through the cylinder wall with respect to the phase of the ultrasonic waves introduced in the cylinder wall, and wherein said step of determining a change in the traveling time of the ultrasonic waves traveling through the cylinder wall due to the wear of the cylinder wall includes adjusting the frequency the ultrasonic waves introduced into the cylinder wall to maintain a null relative phase condition between the ultrasonic waves which have traveled through the cylinder wall and the ultrasonic waves introduced in the cylinder wall, and measuring the changes in the frequency of the ultrasonic waves introduced into the cylinder wall to maintain the null relative phase condition.

* * * * *